(12) United States Patent
Fernandez et al.

(10) Patent No.: US 9,687,233 B2
(45) Date of Patent: *Jun. 27, 2017

(54) SURGICAL STAPLING AND CUTTING APPARATUS—DEPLOYMENT MECHANISMS, SYSTEMS AND METHODS

(71) Applicant: Dextera Surgical Inc., Redwood City, CA (US)

(72) Inventors: Anthony J. Fernandez, San Carlos, CA (US); Bryan D. Knodel, Flagstaff, AZ (US)

(73) Assignee: Dextera Surgical Inc., Redwood City, CA (US)

( * ) Notice: Subject to any disclaimer, the term of this patent is extended or adjusted under 35 U.S.C. 154(b) by 492 days.

This patent is subject to a terminal disclaimer.

(21) Appl. No.: 14/272,285

(22) Filed: May 7, 2014

(65) Prior Publication Data

US 2014/0332578 A1 Nov. 13, 2014

Related U.S. Application Data

(60) Provisional application No. 61/821,493, filed on May 9, 2013.

(51) Int. Cl.
| | |
|---|---|
| *A61B 17/068* | (2006.01) |
| *A61B 17/072* | (2006.01) |
| *A61B 17/064* | (2006.01) |
| *A61B 17/00* | (2006.01) |
| *A61B 17/29* | (2006.01) |

(52) U.S. Cl.
CPC ...... *A61B 17/068* (2013.01); *A61B 17/07207* (2013.01); *A61B 2017/00389* (2013.01); *A61B 2017/0647* (2013.01); *A61B 2017/2902* (2013.01); *A61B 2017/294* (2013.01); *A61B 2017/2923* (2013.01); *A61B 2017/2946* (2013.01)

(58) Field of Classification Search
CPC ................ A61B 17/068; A61B 17/072; A61B 2017/00367; A61B 2017/2923
USPC ........ 227/175.2, 178.1, 180.1; 606/151, 139, 606/219
See application file for complete search history.

(56) References Cited

U.S. PATENT DOCUMENTS

| | | | |
|---|---|---|---|
| 7,121,446 | B2 | 10/2006 | Arad et al. |
| 7,384,421 | B2 | 6/2008 | Husuka |
| 7,832,408 | B2 | 11/2010 | Shelton, IV et al. |

(Continued)

OTHER PUBLICATIONS

International Search Report and Written Opinion, PCT/US2014/037582, mailed Sep. 12, 2014.

*Primary Examiner* — Nathaniel Chukwurah
(74) *Attorney, Agent, or Firm* — Vista IP Law Group, LLP

(57) ABSTRACT

A surgical stapling device is configured for use in open and/or laparoscopic surgical procedures. The device includes a handle assembly, a shaft assembly coupled to the handle assembly, and an end-effector coupled to the shaft assembly. The end-effector comprises of a jaw assembly configured to clamp, staple, and/or cut a target tissue. The handle assembly comprises of a trigger element that can activate a drive assembly to advance a deployment assembly to staple and/or cut the aforementioned target tissue. The deployment assembly comprises of a deployment slide member to either advance the deployment assembly in a first direction or retreat the deployment assembly in a second direction.

23 Claims, 12 Drawing Sheets

(56) References Cited

U.S. PATENT DOCUMENTS

| | | |
|---|---|---|
| 7,967,178 B2 | 6/2011 | Scirica et al. |
| 8,342,378 B2 | 1/2013 | Marczyk et al. |
| 2005/0103819 A1* | 5/2005 | Racenet ........... A61B 17/07207 227/175.1 |
| 2009/0145947 A1* | 6/2009 | Scirica ............. A61B 17/07207 227/175.2 |

* cited by examiner

SURGICAL STAPLING AND CUTTING APPARATUS—DEPLOYMENT MECHANISMS, SYSTEMS AND METHODS

CROSS-REFERENCE TO RELATED APPLICATION(S)

The application claims priority to Provisional U.S. Patent Application No. 61/821,493, filed on May 9, 2013, which is incorporated herein by reference.

FIELD OF THE INVENTION

The present invention relates generally to medical devices, and more particularly to surgical stapling and cutting systems, such as endocutters and microcutters.

BACKGROUND

Traditionally, surgeons use sutures to close wounds and incisions, attach separate tissue structures to one another, and perform other medical or surgical functions in various surgical procedures or operations. However, proper suturing requires significant skills to perform; in particular, complex suturing procedures can be time-consuming and/or very difficult to perform effectively. Furthermore, suturing may be impractical or unfeasible in certain situations. For example, suturing may be very difficult to perform in minimally-invasive surgical procedures where suturing tools may be required to be inserted through a small opening (often referred to as an access port) to gain access into a patient's body, and then the suturing operation is performed through the small access opening with extension tools to suture the target tissue. In such minimally-invasive surgical procedures, the opening or access port to the surgical site inside the patient may not be large enough to allow effective maneuvering of suturing tools to perform the suturing procedure efficiently and effectively. If access ports were made larger to allow for easier suturing operations, the benefits of minimally-invasive surgery, however, may be significantly reduced or altogether eliminated. Indeed, as surgical technology continues to progress, the size of the access ports required to access surgical sites in the body to perform minimally-invasive procedures correspondingly continues to decrease. Presently, micro-laparoscopy typically utilizes instruments with diameter of about 3 millimeters to about 2 millimeters to perform complex operations; e.g., laparoscopic cholecystectomy and inguinal hernia repair, etc. When instruments of such small diameters are used, the size of the access ports may also be very small. It is common that the access ports can be as small as about 3 millimeters to about 2 millimeters in diameters. The benefits of these advances in surgical technology to the patients are obvious, minimally-invasive procedures can cause less physical trauma to the patient. As such, these minimally-invasive procedures can be performed to greater percentage of patients even if they are not in the best physical condition. In addition, because there is generally less physical trauma involved, the patients may experience less discomfort, the recovery time is typically reduced, and there may be less scarring at the operation site. However, because of restricted access, it can be significantly difficult or nearly impossible sometimes to perform effective manual suturing within a patient's body through these small access ports in minimally-invasive procedures. As such, alternatives to suturing or manual suturing are highly desired.

SUMMARY OF THE INVENTION

A surgical stapling device is configured for use in open and/or laparoscopic surgical procedures. The device includes a handle assembly, a shaft assembly coupled to the handle assembly, and an end-effector coupled to the shaft assembly. The end-effector comprises of a jaw assembly configured to clamp, staple, and/or cut a target tissue. The handle assembly comprises of a trigger element that can activate a drive assembly to advance a deployment assembly to staple and/or cut the aforementioned target tissue. The deployment assembly comprises of a deployment slide member to either advance the deployment assembly in a first direction or retreat the deployment assembly in a second direction. Furthermore, a swing arm member is movably coupled to the deployment assembly that is configured to reset a clamp lock member to release the jaw assembly to an un-clamp state. The swing arm member additionally configured to reset a deploy release member to allow a mode switch member to be reset to a neutral state to disengage the drive assembly from a deploy mode to the neutral mode.

A surgical stapling device comprises of a mode switch member to select a drive assembly to a deployment mode and a trigger member to activate the drive assembly to advance a deployment assembly to staple and cut a target tissue. The surgical device also includes a deployment slide member to advance the deployment assembly in a first direction to drive both a wedge assembly to deploy staples into the target tissue and a knife member to cut the target tissue. The surgical device further includes a swing arm member with a reset tab element to release a clamp lock to unclamp a jaw assembly to release the target tissue and to reset the mode switch member to a neutral state to disengage the drive assembly from the deployment mode.

A surgical stapling device comprises a mode switch member to select a drive assembly to a deployment mode and a trigger member to activate the drive assembly to advance a deployment assembly to staple a target tissue. The surgical stapling device also includes a deployment slide member to advance the deployment assembly in a first direction to drive a wedge assembly to deploy staples into the target tissue. The surgical device further includes a swing arm member with a reset tab element to release a clamp lock to unclamp a jaw assembly to release the target tissue and to reset the mode switch member to a neutral state to disengage the drive assembly from the deployment mode.

A method of stapling and cutting tissue by a surgical stapling device. The method comprises setting a mode switch member to engage a drive assembly to a deployment mode to initiate deployment. The method also includes activating a trigger member to drive the drive assembly and advancing a deployment slide member of a deployment assembly. The method then involves urging forward by the deployment assembly a wedge assembly to deploy staples in a target tissue and urging forward by the deployment assembly a knife member to cut said target tissue. The method further includes placing a swing arm member with a reset tab element in a first reset position to release a clamp lock to unclamp a jaw assembly, and placing the swing arm member in a second reset position to release a deployment release member to reset the mode switch member to neutral state to disengage the drive assembly from deployment mode.

A surgical stapling device comprises a handle assembly, a shaft assembly coupled to the handle assembly, and an end-effector coupled to the shaft assembly. The end-effector comprises a jaw assembly configured to clamp, staple, and cut a target tissue. The handle assembly comprises a trigger element to activate a drive assembly to advance a deployment assembly to staple and cut the target tissue. The deployment assembly comprises a deploy slide member to either advance the deployment assembly in a first direction or retreat said deployment assembly in a second direction, and a reset switch member configured to retread the deployment assembly to a first reset position causing an unclamp tab element of a swing arm member to release a clamp lock member from a clamp lock state. The reset switch member further configured to retreat said swing arm member without displacing said deployment assembly to cause the unclamp tab element to engage a deployment release member to reset a mode switch button from a deployment mode.

A surgical stapling device comprises a mode switch member to select a drive assembly to a deployment mode and a trigger member to activate the drive assembly to advance a deployment assembly to staple and cut a target tissue. The surgical stapling device further includes a deployment slide member to advance the deployment assembly in a first direction to drive both a wedge assembly to deploy staples into the target tissue and a knife member to cut the target tissue. The surgical device also includes a reset switch member to place a swing arm member with a reset tab element in a first reset position to release a clamp lock member to unclamp a jaw assembly to release the target tissue and to further place the swing arm member in a second reset position without causing displacement of the deployment assembly to release a deployment reset member.

A surgical stapling device comprises a mode switch member to select drive assembly to a deployment mode and a trigger member to activate the drive assembly to advance a deployment assembly to staple a target tissue. The surgical stapling device also includes a deployment slide member to advance the deployment assembly in a first direction to drive a wedge assembly to deploy staples into the target tissue and a reset switch member to place a swing arm member with a reset tab element in a first reset position to release a clamp lock member to unclamp a jaw assembly to release the target tissue and to further place the swing arm member in a second reset position without causing displacement of the deployment assembly to release a deployment to release a deployment reset member.

A method of stapling and cutting tissue by a surgical device comprises of setting a mode switch member to engage a drive assembly to a deployment mode and activating a trigger member to drive the drive assembly. The method further includes advancing a deployment slide member of a deployment assembly, urging forward by the deployment assembly a wedge assembly to deploy staples in a target tissue, and urging forward by the deployment assembly a knife member to cut the target tissue. The method also includes placing a swing arm member with a reset tab element in a first reset position to release a clamp lock to unclamp a jaw assembly and placing the swing arm member in a second reset position, without causing displacement to the deployment assembly, to release a deployment release member to reset the mode switch member to a neutral state to disengage the drive assembly from deployment.

A surgical stapling device comprises a handle assembly, a shaft assembly coupled to the handle assembly, and an end-effector coupled to the shaft assembly. The end-effector includes a jaw assembly configured to clamp, staple and cut a target tissue. The handle assembly includes a trigger element to activate a drive assembly to advance a deployment assembly to staple and cut the target tissue. The deployment assembly includes a deployment slide member to either advance the deployment assembly in a first direction or retreat the deployment assembly in a second direction. The surgical stapling device further includes a reset switch member configured to retreat the deployment assembly to a first reset position causing an unclamp tab element of a swing arm to engage a deployment release member to reset a mode switch member from a deployment mode, and the reset switch member further configured to retreat the swing arm member to cause the unclamp tab element to engage a clamp lock member from a clamp lock state to release the jaw assembly from a clamped state.

A surgical stapling device comprises a mode switch member to select a drive assembly to a deployment mode and a trigger member to activate the drive assembly to advance a deployment assembly to staple and cut a target tissue. The surgical stapling device also includes a deployment slide member to advance the deployment assembly in a first direction to drive both a wedge assembly to deploy staples into the target tissue and a knife member to cut the target tissue. The surgical stapling device also includes a reset switch member to place a swing arm member with a reset tab element in a first reset position to release a deployment reset member and to further place the swing arm member in a second reset position to release a clamp lock member to unclamp a jaw assembly to release the target tissue.

A surgical stapling device comprises a mode switch member to select a drive assembly to a deployment mode and a trigger member to activate the drive assembly to advance a deployment assembly to staple a target tissue. The surgical device also includes a deployment slide to advance the deployment assembly in a first direction to drive a wedge assembly to deploy staples into the target tissue, and a reset switch member to place a swing arm member with a reset tab element in a first position to release a deployment reset member and to further place the swing arm member in a second reset position to release a clamp lock member to unclamp a jaw assembly to release the target tissue.

A method of stapling and cutting tissue by a surgical stapling device comprises of setting a mode switch member to engage a drive assembly to deployment mode for deployment and activating a trigger member to drive the drive assembly. The method also includes urging forward by the deployment assembly a wedge assembly to deploy staples in a target tissue, urging forward by the deployment assembly a knife member to cut the target tissue and placing a deployment release member to reset the mode switch member to a neutral state to disengage the drive assembly from deployment. The method may further include placing the swing arm member in a second reset position to release a clamp lock member to unclamp a jaw assembly to disengage the target tissue.

BRIEF DESCRIPTION OF THE DRAWINGS

The present invention will be readily understood by the following detailed description, taken in conjunction with accompanying drawings, illustrating by way of examples of the invention. The objects and elements in the drawings are not necessarily drawn to scale, proportion, precise orientation or positional relationships; instead, emphasis is focused on illustrating the principles of the invention. The drawings illustrate the design and utility of various features, aspects, or embodiments of the present invention, in which like element are referred to by like reference symbols or numerals. The drawings, however, depict the features, aspects, or embodiments of the invention, and should not be taken as limiting in their scope. With this understanding, the features, aspects, or embodiments of the invention will be described and explained with specificity and details through the use of the accompanying drawings in which.

As can be appropriated, the use of same or similar symbols or numerals in different figures indicates similar or identical items or features.

DETAILED DESCRIPTION

Figure 1A:
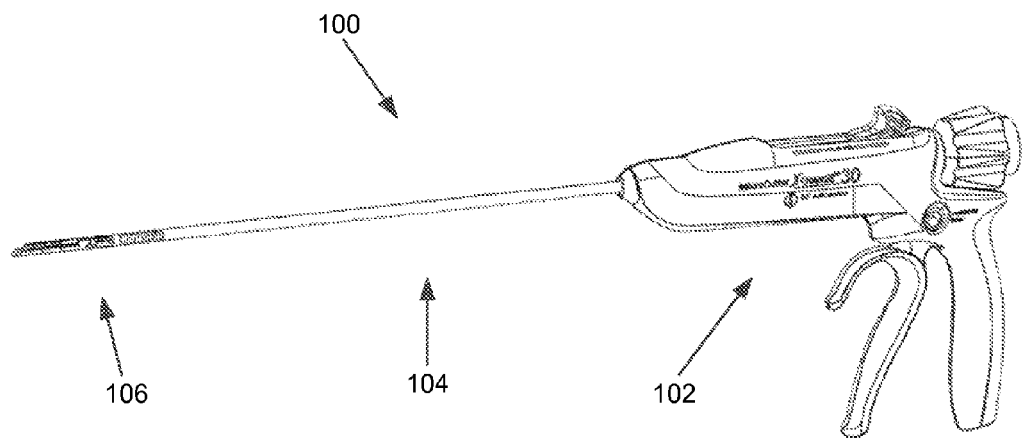
FIG. 1A and FIG. 1B illustrate an example of a surgical stapling and cutting device where the deployment mechanisms in accordance with features, aspects, or embodiments of the present invention may be used to deploy various components to staple and cut tissue at a surgical site of a patient.

In the following detailed description, specific details are set forth in order to provide a thorough understanding of the present invention. However, it will be readily understood by those skilled in the art that the present invention may be practiced without these specific details. Alternatively, some of the well-known parts, component, hardware, methods of operations, and procedures may not be described in detail or elaborated so as to avoid obscuring the present invention; but, nevertheless, they are within the spirit and scope of the present invention.

As mentioned, surgeons use sutures to close wounds and incisions, attach separate tissue structures to one another, and perform other medical or surgical functions in various surgical procedures or operations. However, proper suturing requires significant skills to perform; in particular, complex suturing procedures can be time-consuming and/or very difficult to perform effectively. Furthermore, suturing may be impractical or unfeasible in certain situations. For example, suturing may be very difficult to perform in minimally-invasive surgical procedures where suturing tools may be required to be inserted through a small opening (often referred to as an access port) to gain access into a patient's body, and then the suturing operation is performed through the small access opening with extension tools to suture the target tissue. In such minimally-invasive surgical procedures, the opening or access port to the surgical site inside the patient may not be large enough to allow effective maneuvering of suturing tools to perform the suturing procedure efficiently and effectively. If access ports were made larger to allow for easier suturing operations, the benefits of minimally-invasive surgery, however, may be significantly reduced or altogether eliminated. Indeed, as surgical technology continues to progress, the size of the access ports required to access surgical sites in the body to perform minimally-invasive procedures correspondingly continues to decrease. Presently, micro-laparoscopy typically utilizes instruments with diameter of about 3 millimeters to about 2 millimeters to perform complex operations; e.g., laparoscopic cholecystectomy and inguinal hernia repair, etc. When instruments of such small diameters are used, the size of the access ports may also be very small. It is common that the access ports can be as small as about 3 millimeters to about 2 millimeters in diameters. The benefits of these advances in surgical technology to the patients are obvious, minimally-invasive procedures can cause less physical trauma to the patient. As such, these minimally-invasive procedures can be performed to greater percentage of patients even if they are not in the best physical condition. In addition, because there is generally less physical trauma involved, the patients may experience less discomfort, the recovery time is typically reduced, and there may be less scarring at the operation site. However, because of restricted access, it can be significantly difficult or nearly impossible sometimes to perform effective manual suturing within a patient's body through these small access ports in minimally-invasive procedures.

Figure 1B:
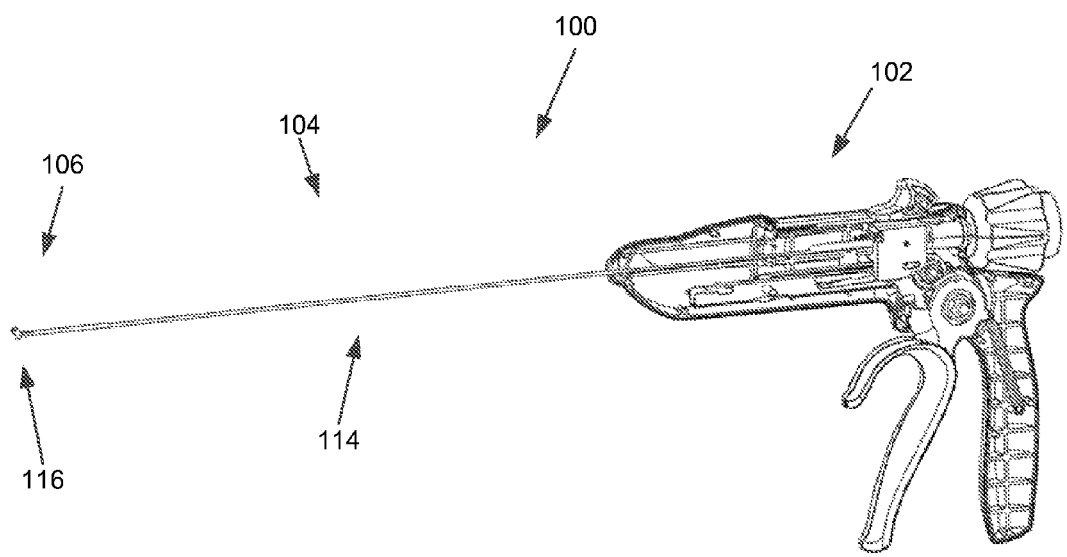

FIG. 1A and FIG. 1B illustrate an example of a surgical stapling and cutting device 100 that can be an alternative or replacement to suturing. In particular, this example of surgical stapling and cutting device 100 is especially useful for replacing suturing in minimally-invasive surgical procedures. Similarly, it can also be used in open surgeries. While this example of surgical stapling and cutting device is designed and constructed to perform stapling and cutting of tissue, the design and construction can easily be altered to include more or less functions. For example, the design and construction can be altered to perform stapling function without cutting of tissue (e.g., a knife element can be removed and/or replaced). As illustrated in the figures, the operation of stapling and cutting is performed through a long slim shaft 104 and a similarly slim end-effector 106. The actual operations of clamping, stapling, and cutting of tissue are performed at the distal-end 106 of the shaft 104. Further illustrated, a portion of the shaft 104 at the distal-end may be substantially flexible and may be articulated. Various versions of the endo-cutter or micro-cutter stapling systems may have non-articulated rigid shafts, while other versions may include substantially flexible or flexible portions that can be articulated. These and other features allow such examples of surgical stapling and cutting devices (e.g., MICROCUTTER XPRESS® and MICROCUTTER XCHANGE®, which are designed and manufactured by Cardica Inc. of U.S.A.) to be ideally suited as alternatives or replacements to suturing. Greater detailed discussions of surgical stapling and cutting systems are described in U.S. patent application Ser. No. 12/323,309, filed on Nov. 25, 2008; U.S. patent application Ser. No. 12/400,760, filed on Mar. 9, 2009; U.S. patent application Ser. No. 12/400,790, filed on Mar. 9, 2009; U.S. patent application Ser. No. 12/477,065, filed on Jun. 2, 2009; U.S. patent application Ser. No. 12/787,708, filed on May 26, 2010; U.S. patent application Ser. No. 13/093,791, filed on Apr. 25, 2011; U.S. patent application Ser. No. 12/477,302, filed on Jun. 3, 2009; U.S. patent application Ser. No. 12/489,397, filed on Jun. 22, 2009; U.S. patent application Ser. No. 12/612,614, filed on Nov. 4, 2009; U.S. patent application Ser. No. 12/840,156, filed on Jun. 20, 2010; U.S. patent application Ser. No. 13/028,148, filed on Feb. 15, 2011; U.S. patent application Ser. No. 13/048,674, filed on Mar. 15, 2011; U.S. patent application Ser. No. 13/094,716, filed on Apr. 26, 2011; U.S.

patent application Ser. No. 13/094,805, filed on Apr. 26, 2011; U.S. patent application Ser. No. 13/093,743, filed on Apr. 25, 2011; U.S. patent application Ser. No. 13/105,799, filed on May 11, 2011; and U.S. patent application Ser. No. 13/294,160, filed on Nov. 10, 2011, all of which are incorporated herein by reference.

Still referring to FIG. 1A and FIG. 1B, the surgical stapling and cutting device 100 includes a handle assembly 102, a shaft assembly 104, and an end-effector 106 coupled to the shaft assembly 104. During a deployment operation, a knife element 116 is advanced by a deployment strip 114 to cut tissue. FIG. 1B illustrates an exposed view of the surgical stapling and cutting device 100 to show some of the deployment mechanisms and components involved with effecting stapling and cutting operations of the surgical device 100. In an alternative configuration, the knife element 116 can be removed and/or replaced such that device 100 can perform stapling functions without cutting tissue.

Figure 2A:
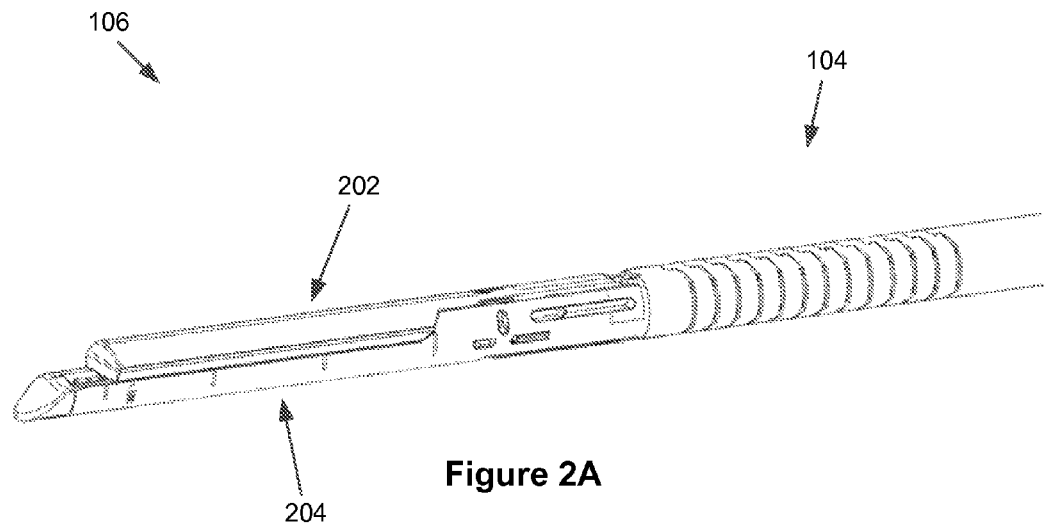
FIG. 2A through FIG. 2F illustrate an end-effector of a surgical stapling and cutting device where the deployment mechanisms in accordance with features, aspects, or embodiments of the present invention may be used to deploy various components to staple and cut tissue at a surgical site of a patient.
Figure 2B:
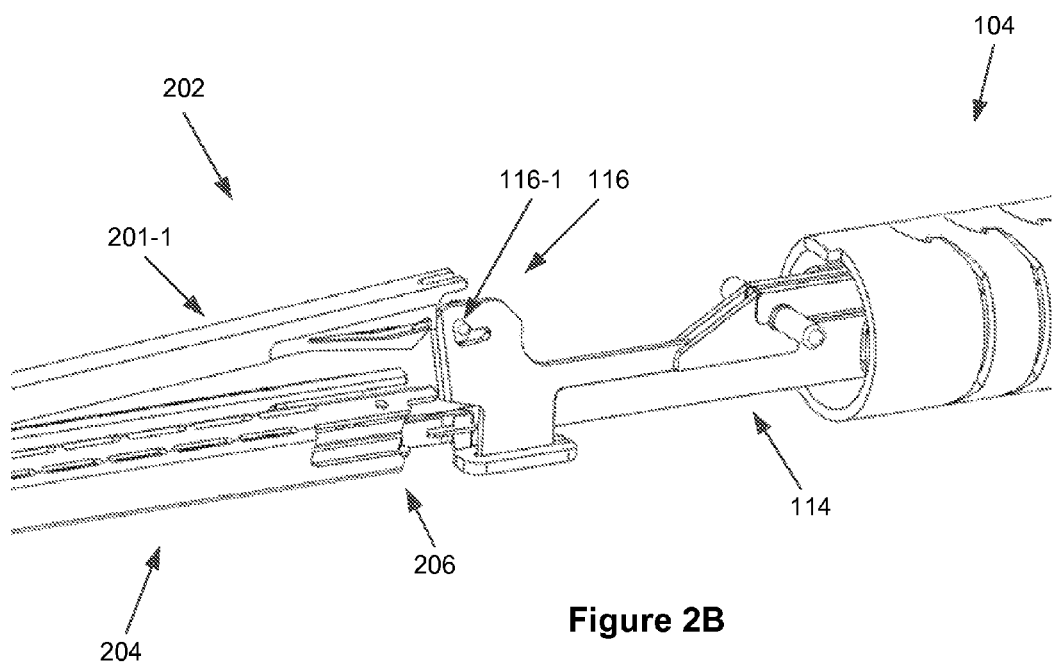
Figure 2C:
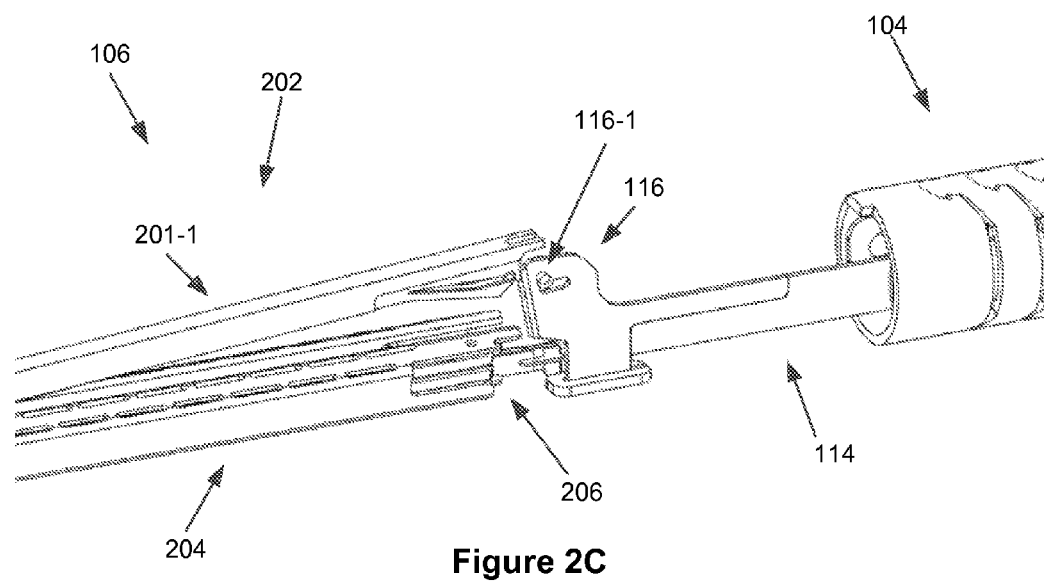
Figure 2D:
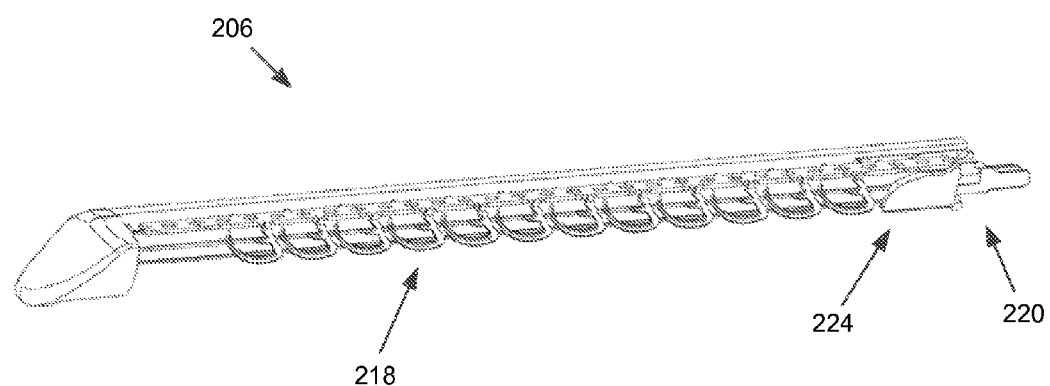
Figure 2E:
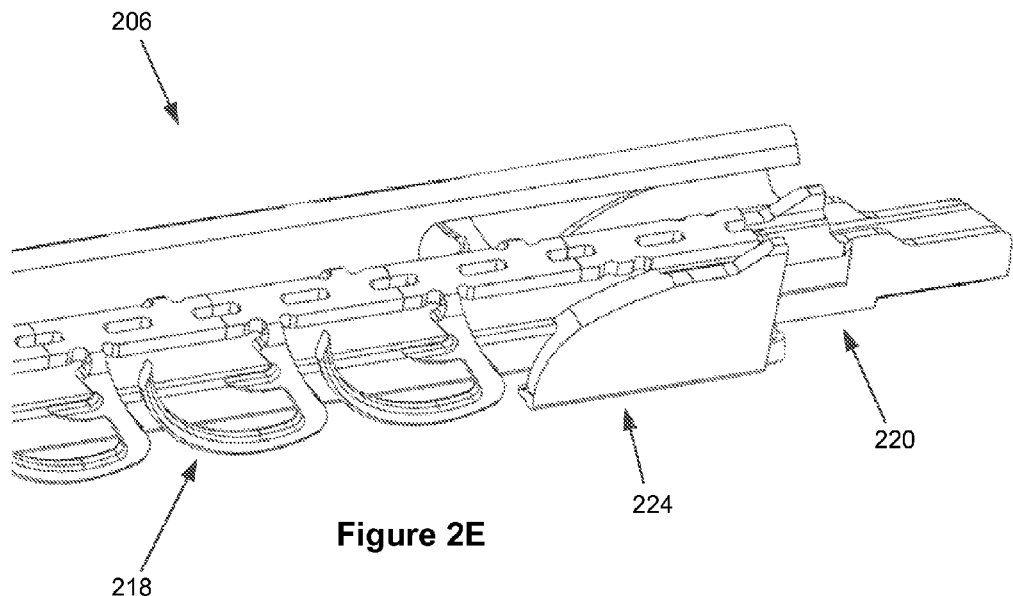
Figure 2F:
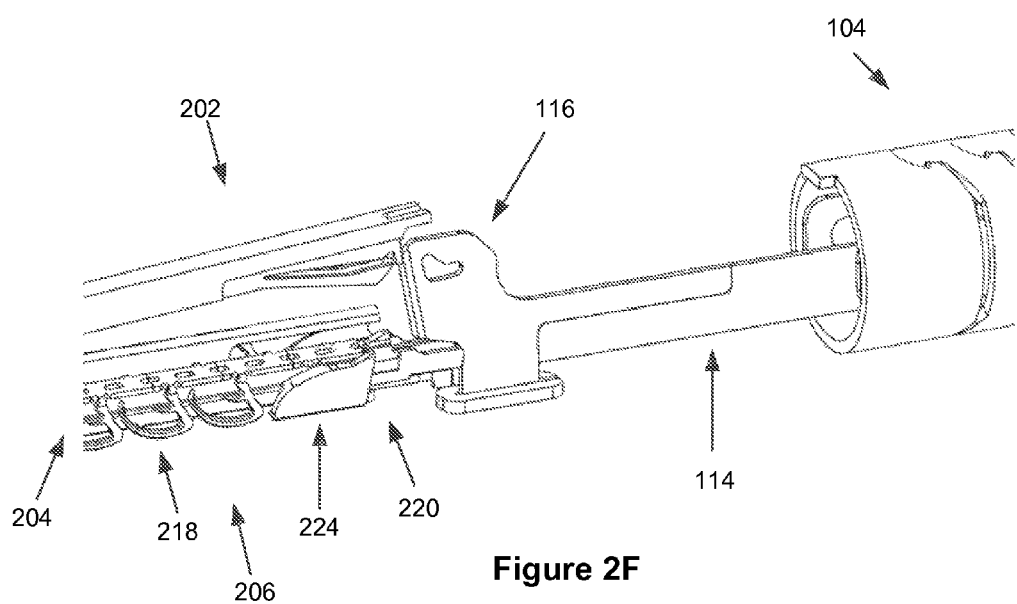

FIG. 2A through FIG. 2F illustrate an end-effector 106 of a surgical stapling and cutting device 100 where the deployment mechanisms in accordance with features, aspects, or embodiments of the present invention may be used to deploy various components to staple and cut tissue at a surgical site of a patient. As illustrated in FIG. 2A, the end-effector 106 comprises of a jaw assembly which includes a staple channel member 204 for holding a staple cartridge member 206 where staples 218 are delivered and deployed, and an anvil member 202 for receiving and deforming the deployed staples 218. For additional details of the anvil member 202, FIG. 2B and FIG. 2C illustrate an anvil insert 202-1, which is part of the anvil member 202, which interacts with an I-beam pin 116-1 of the knife member 116 to maintain a clamp gap between the anvil member 202 and the staple channel member 204. FIG. 2D illustrates an exposed view of the staple cartridge member 206 to show the staples 218 and a wedge assembly 220 with one or more wedge elements 224 for deploying the staples 218. The anvil member 202 may include staple forming pockets on its under-surface to encounter and deform the deployed staples 218 from the staple cartridge member 206. As will be discussed in more detail, the wedge assembly 220 is advanced by the deployment strip member 114 (typically with the knife member 116 coupled to the distal portion of the deployment strip member 114) to act against each of the respective staples 218 to cause each of the staples 218 to be deployed in a substantially forward and upward motion to engage tissue that is positioned and/or clamped between the staple cartridge member 206 and the anvil member 202. As can be appreciated from the illustrated figures, as the wedge assembly 220 is advanced by the deployment strip member 114, the wedge element 224 acts against a staple 218 and pushes it forward and upward in an arcuate path, see FIG. 2B through FIG. 2F. Unlike conventional stapling systems, the wedge element 224 acts directly on a staple 218. For example, conventional stapling systems include a staple driver member that holds a staple, and a wedge member acts on the staple driver member. The conventional wedge member drives the staple holder and the staple in a substantially linearly upward direction into tissue and against an anvil member that deforms the conventional staple. As should be noted further, unlike conventional stapling systems, each of the staples 218 undergoes an arcuate motion as it is being deployed, not a linear motion. The forced motion of the staple 218 by the wedge element 224 causes each of the staples 218 to be frangibly separated from its connection or attachment point. Each of the deployed staples 218 encounters a corresponding staple forming pocket on the under-surface of the anvil member 202, in which each of the deployed staples 218 will be deformed into a closed configuration securing the target tissue and leaving it in a hemostasis condition (after it has been cut by the knife member 116).

Figure 3A:
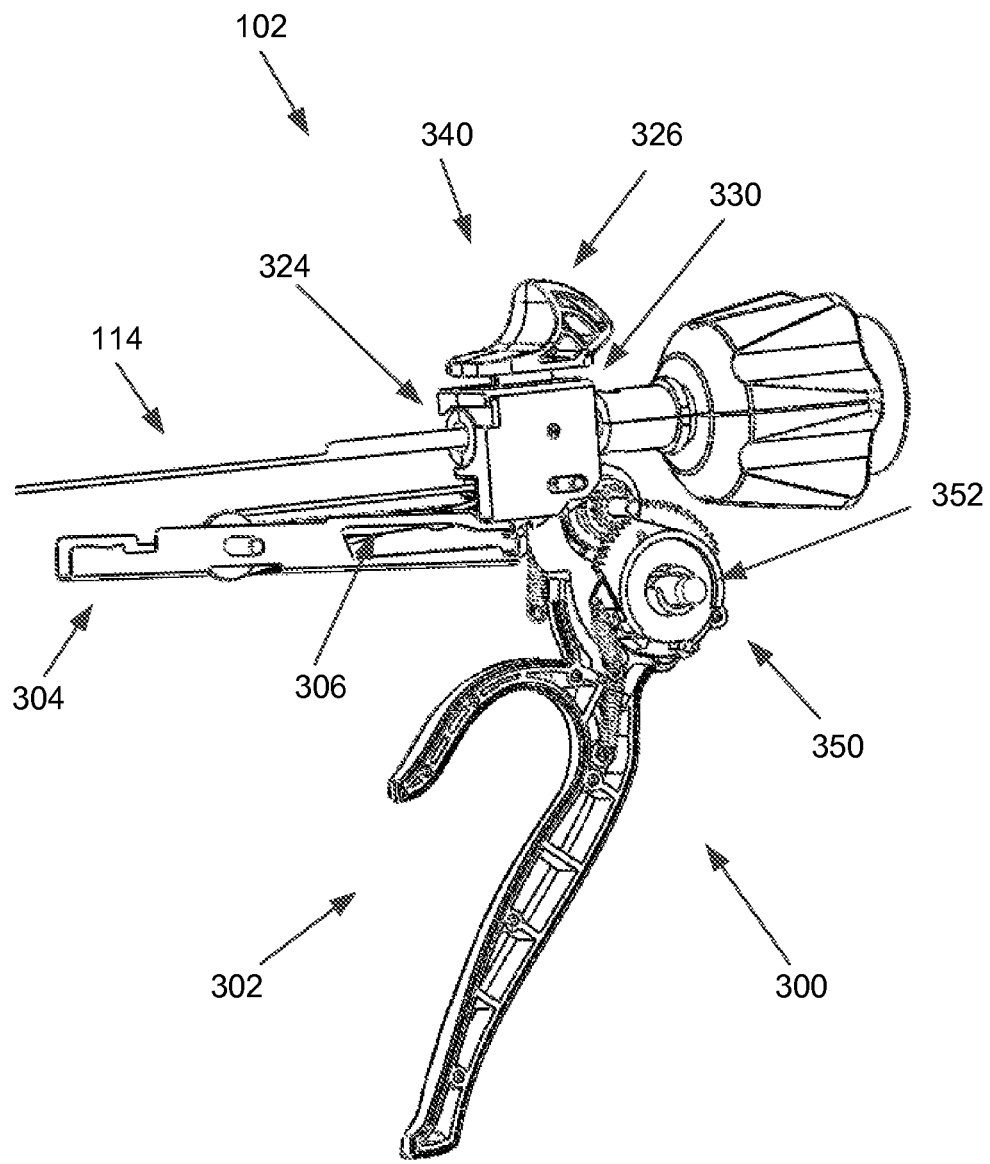
FIG. 3A and FIG. 3B illustrate some of the deployment mechanisms of a surgical stapling and cutting device in accordance with features, aspects, or embodiments of the present invention.
Figure 3B:
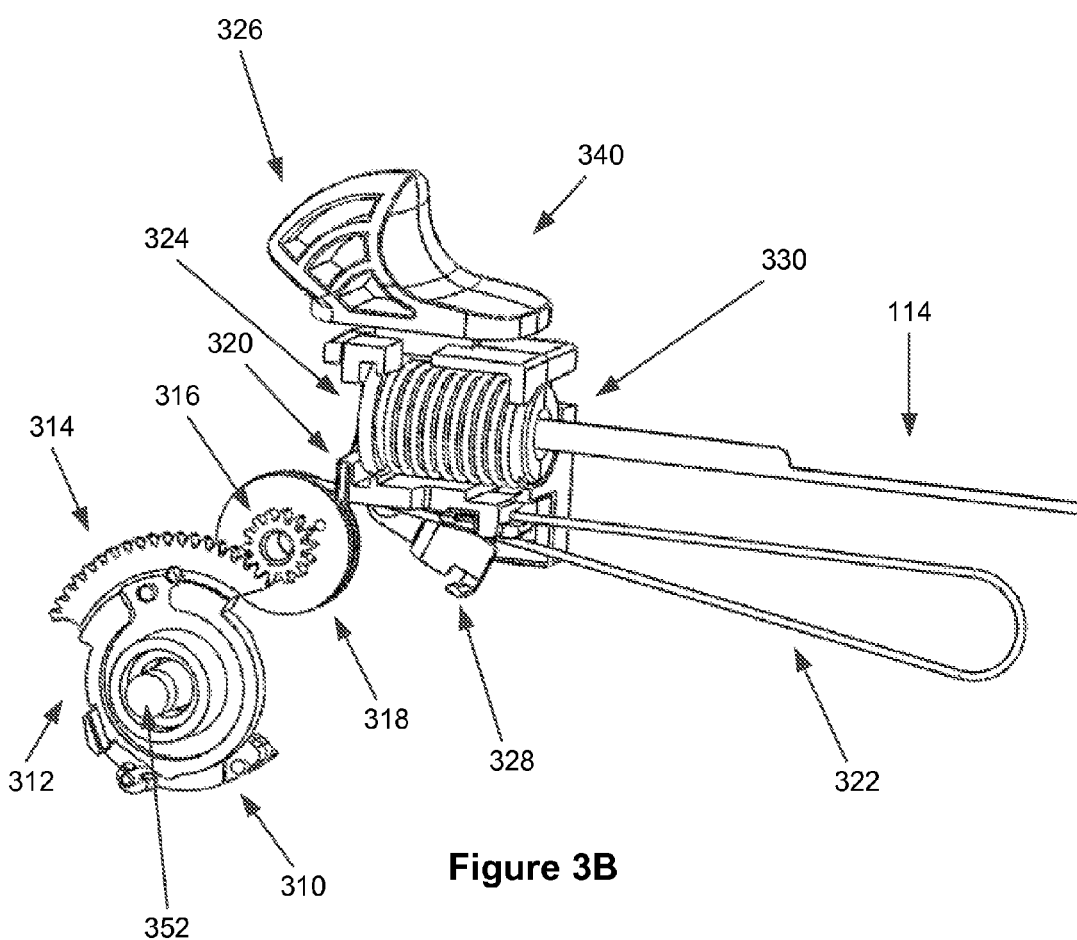

FIG. 3A and FIG. 3B illustrate the deployment mechanisms of the surgical stapling and cutting device 100. The deployment mechanisms may include a trigger assembly 300 coupled to a gear assembly 350 to drive various handle and shaft mechanisms, components, and elements for clamping, stapling, and cutting of tissue. Typically, the surgical stapling and cutting device 100 can be put into at least two modes of operation; a clamp mode and a deployment mode. The modes of operation can be selected by a mode switch button 352. The clamp mode usually involves operating the various mechanisms, components, and elements for clamping a target tissue prior to or in preparation of stapling and cutting the target tissue by the surgical device 100. The deployment mode usually involves operating the various mechanisms, components, and elements for stapling and cutting the target tissue by the surgical device 100.

Referring to FIG. 3A and FIG. 3B, the mode switch button 352 may be selected to place the surgical device 100 into a clamp mode or a deployment mode. In the deployment mode, a ratchet member 310 is selected or activated to engage with a trigger member 302 and a gear member 312. Upon activation of the trigger member 302 by the attending surgeon, the trigger member 302 drives the gear assembly 350 which involves starting the gear member 312, gear member 314, gear member 316, and pulley member 318 to activate a deployment cable member 322 to advance the deployment assembly 340. The deployment assembly 340 comprises of a deployment slide member 320, a deployment spool member 324, a reset switch member 326, and a deployment strip member 114. The slide member 320 may be configured as a carrier member for the spool member 324 and reset switch member 326. The deployment cable 322 may advance the deployment assembly 340 in a first direction by pulling onto the slide member 320. For example, the attending surgeon may activate the trigger member 302, during deployment mode, to advance the deployment assembly 340 to a first deployment position. The attending surgeon may activate the trigger member 302 again to advance the deployment assembly 340 to a second deployment position. Alternatively, the attending surgeon may retract the deployment assembly 340 in a second direction by pulling onto the reset switch member 326 to reset the deployment assembly 340, instead of continuing deployment (e.g., stapling additional portion of the target tissue and cutting additional portion of the target tissue). The retraction or retreat of the deployment assembly 340 from a first deployment position to a first retracted position may cause the unclamp tab element 328 to engage and release the deployment release member 306 to release the drive assembly 350 from the deployment mode. The deployment release member 306 may include stepwise features or ramp-wise features (as illustrated in FIG. 3A) to facilitate engagement with the unclamp tab element 328 in a retraction or retreat motion, but not in the deployment or forward motion of the deployment assembly 340.

Furthermore, the deployment spool member 324 and deployment reset switch member 326 may have independent degrees of movement separate from the deployment slide member 320, such that a least some portion of the deployment assembly 340 may be "drawn back" further by pulling onto the reset switch member 326 depressing the spool member 324. For example, the reset switch member 326 may not be directly linked or coupled to the spool member 324. As such, the reset switch member 326 may have one or more independent degrees of movement separate from the spool member 324 and/or the deployment slide member 320. The spool member 324 may include a spring element to allow further movement of a portion of the deployment assembly 340 that may be independent of deployment slide member 324 (e.g., the reset switch member 326). The deployment assembly 340 may include a cover member 330 (which may be detachable) that allows a swing arm member 332 (illustrated in FIG. 4D) with an unclamp tab element 328 to move or rotate in a substantially unrestricted or a directed path to engage or disengage with certain members or elements (e.g., the clamp lock member 304, deployment reset member 306) to reset clamping and/or deployment, especially when the reset switch member 326 is drawn back further—depressing the spool member 324. For example, the reset switch member 326 may be used to pull the deployment assembly 340 back to a reset position. The swing arm member 332 and the unclamp tab element 328 may be in a first reset position to engage the clamp lock member 304 to release it from a clamp lock state. A second pull of the reset switch member 326 may depress the spool member 324 to draw the reset switch member 326 and the cover member 330 back further without causing movement or displacement of the deployment assembly 340. The additional movement of the reset switch member 326 and the cover member 330 may cause the swing arm member 332 and the unclamp tab element 328 to be place in a second reset position to engage the deployment release member 306, which then engages with the ratchet member 310 to cause reset of the mode switch button 352. Alternatively, placing the deployment assembly 340 in the first reset position by the reset switch member 326 may not cause the unclamp element tab 328 to engage with the clamp lock member 304 and/or the deployment release member 306. Instead, it may require the reset switch member 326 to be pulled and compressed the spool member 324 to place the unclamp tab element 328 in a second reset position in order to engage and release both the clamp lock member 304 and the deployment release member 306.

The advancement of the deployment strip member 114 drives a knife member 116 and a wedge assembly 220 into motion. The advancement of the deployment strip member 114 causes the wedge member 224 of the wedge assembly 220 to engage and deploy the staples 218 in the cartridge member 206 and the knife member 116 to cut the clamped tissue between the staple cartridge 206 and anvil 202.

Figure 4A:
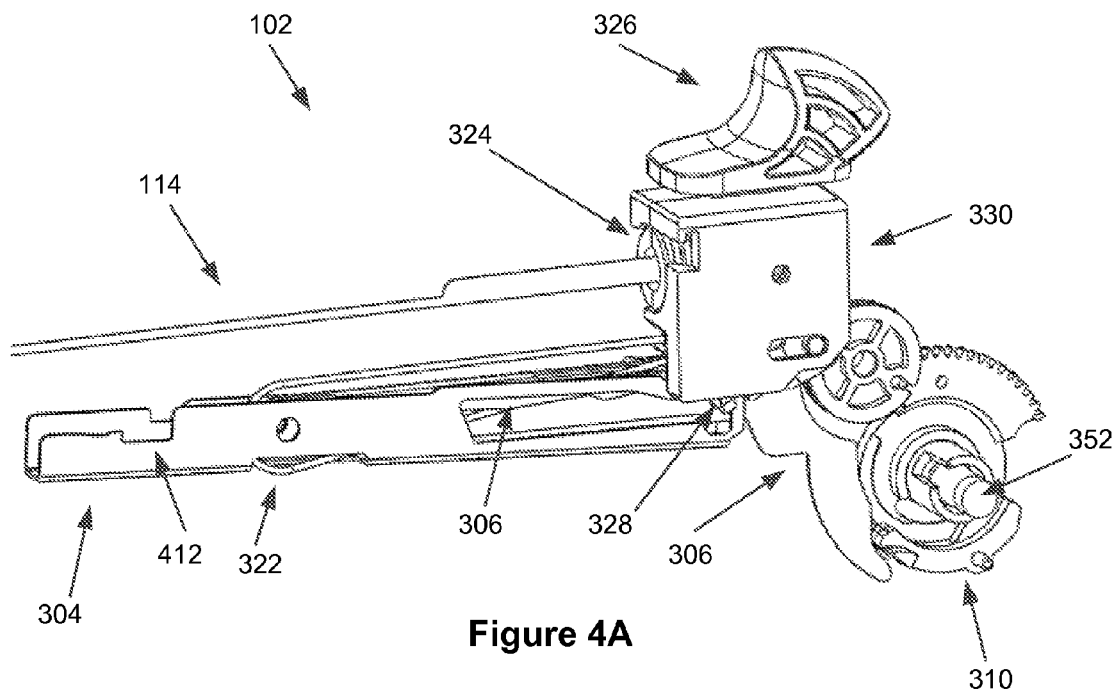
FIG. 4A through FIG. 4D illustrate deployment mechanisms of a surgical stapling and cutting device in accordance with features, aspects, or embodiments of the present invention.
Figure 4B:
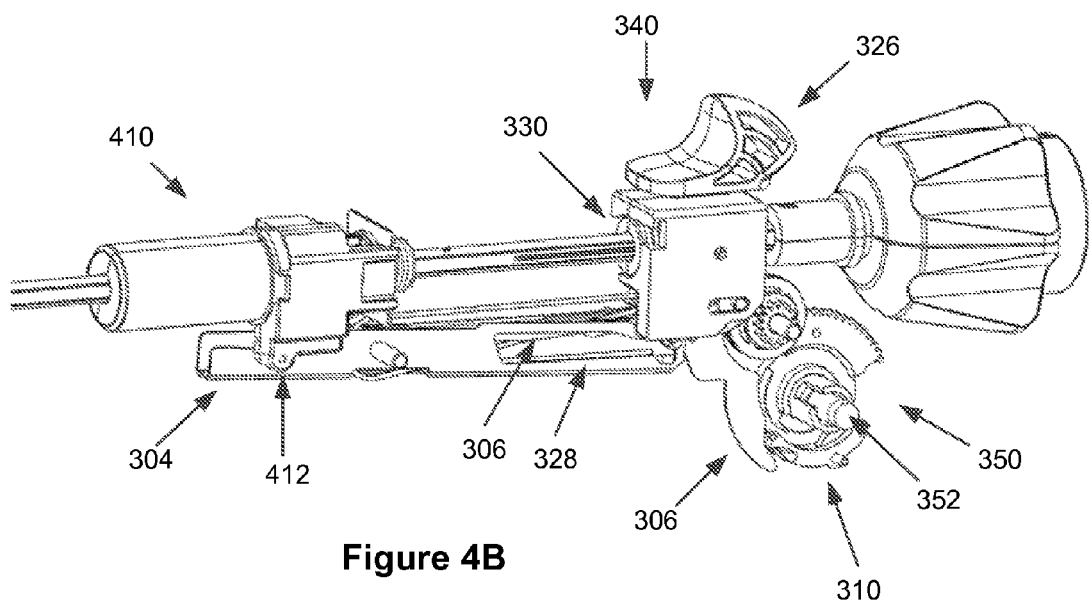
Figure 4C:
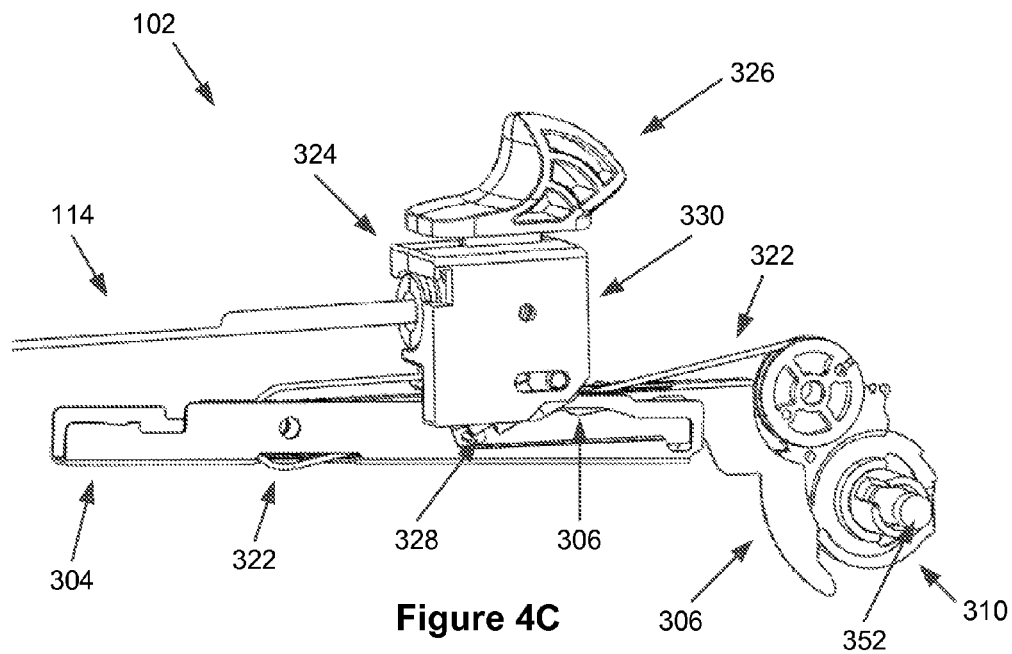
Figure 4D:
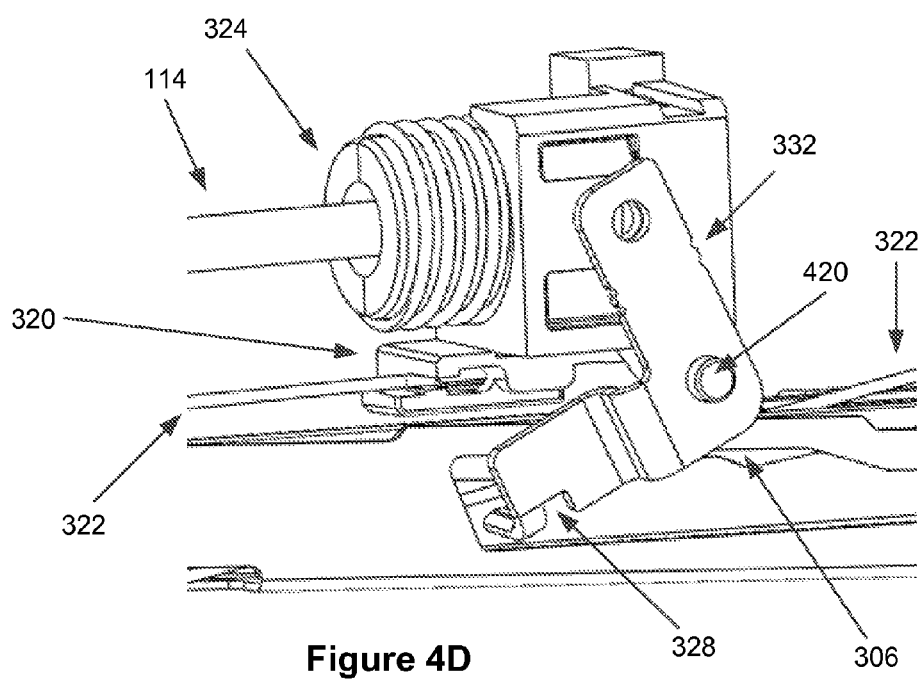

FIG. 4A illustrates the surgical device 100 in a ready deployment position. In this ready deployment position, the deployment assembly 340 may be in a first initial position. In this first initial position, the swing arm member 332 and the unclamp tab element 328 may be in their neutral states (e.g., hanging substantially freely). As such, the unclamp tab element 328 does not engage with the clamp lock member 304 or the deployment release member 306. FIG. 4B further illustrates that the clamp mechanism assembly 410 is placed in a clamp lock position on the clamp lock member 304. In this configuration, the jaw assembly has clamped on a target tissue by the anvil member 202 and staple cartridge member 206. The clamp lock member 306 is maintaining the jaw assembly in a clamped configuration by maintaining the clamp mechanism assembly 410 in the clamp lock pocket element 412. Also illustrated in FIG. 4B, the deployment assembly 340 is in a second position, for example, after a first activation of the trigger member 302 by the operating surgeon. In this second position, the swing arm member 332 and the unclamp tab element 328 are in their neutral states (e.g., hanging substantially freely). As such, the unclamp tab element 328 does not engage with the clamp lock member 304 or the deployment release member 306. To be more clear, typically, a target tissue is clamped by the jaw assembly prior to deployment of the deployment assembly 340. FIG. 4C illustrates the deployment assembly 340 in a third position, for example, after a second activation of the trigger member 302 by the operating surgeon. In this third position, the swing arm member 332 and the unclamp tab element 328 are in their neutral states (e.g., hanging substantially freely). As such, the unclamp tab element 328 does not engage with the clamp lock member 304 or the deployment release member 306. FIG. 4D illustrates the deployment assembly 340 without the deployment assembly cover member 330. As illustrated, the swing arm member 332 and the unclamp tab element 328 are in their neutral states (e.g., hanging substantially freely). As such, the unclamp tab element 328 does not engage with the clamp lock member 304 or the deployment release member 306. However, as illustrated, the swing arm member 332 may pivot about pivot pin 420. When pivoted about pin 420, the unclamp tab element 328 may engage and release the clamp lock member 304 and the deployment release member 306. As will be described in more detail, when the unclamp tab element 328 engages and releases the deployment release member 306, the deployment release member 306 engages with the ratchet member 310 to allow the mode switch button to reset and disengages the deployment drive assembly 350 from the deployment mode.

Figure 5A:
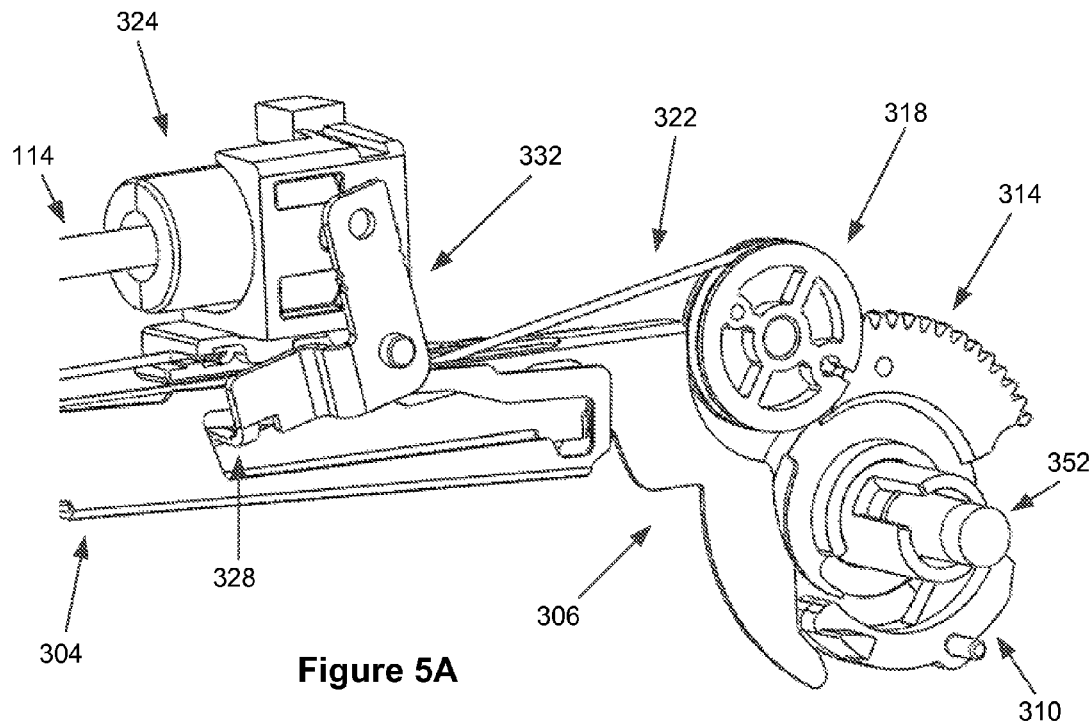
FIG. 5A through FIG. 5H illustrate additional deployment mechanisms of a surgical stapling and cutting device in accordance with features, aspects or embodiments of the present invention.
Figure 5B:
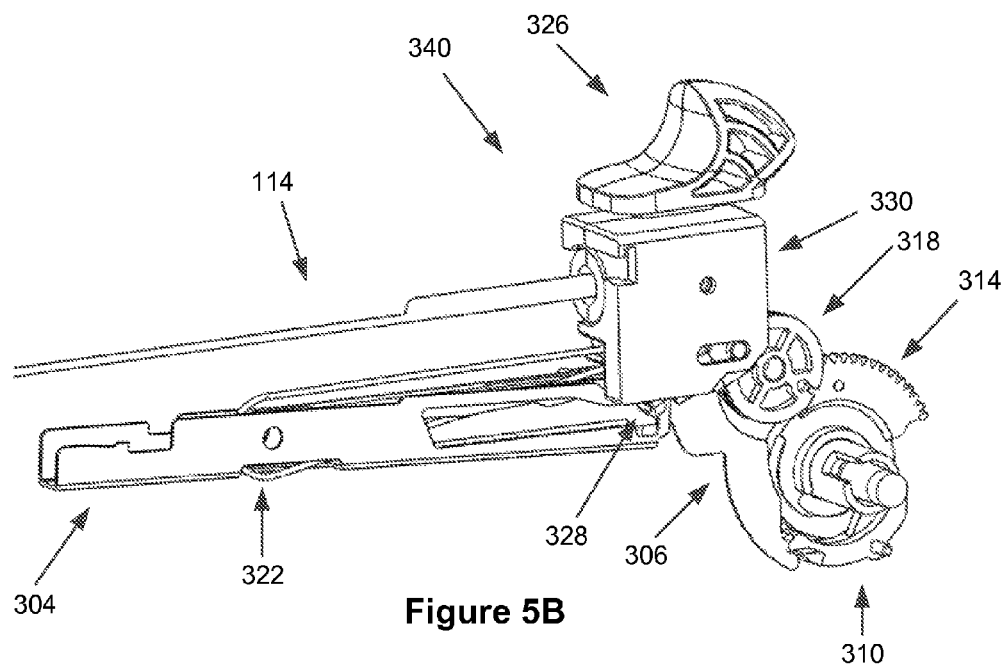
Figure 5C:
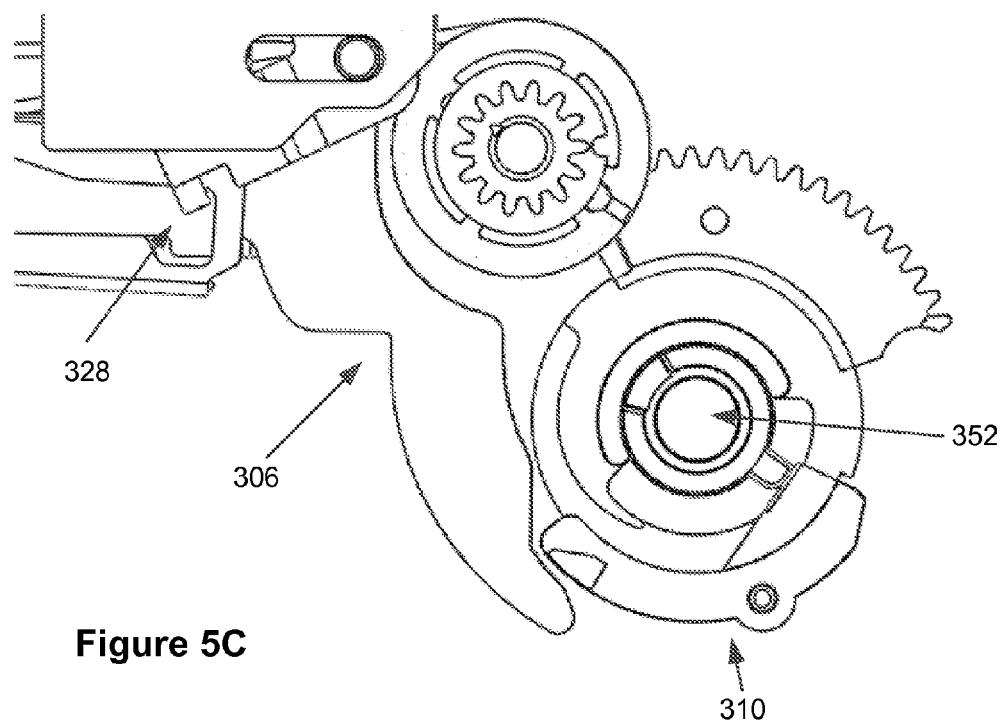

FIG. 5A through FIG. 5H illustrate the deployment assembly 340 being reset to its first position and the mode switch 352 being reset to a neutral state or non-mode position. Starting this discussion with the deployment assembly 340 at the third position of deployment, the unclamp tab element 328 of the swing arm member 332 does not contact or engage with the clamp lock member 304, as illustrated in FIG. 5A. In FIG. 5B, the deployment assembly is retracted or pulled back by way of the reset switch handle 326 to a reset position. The deployment assembly 340 is in a first retracted or reset position. In this position, the reset tab 328 of the swing arm member 332 engages with the proximal portion of the clamp lock member 304 and lifts the proximal portion of the clamp lock member 304 "upward". The upward movement of the proximal port of the clamp lock member 304 causes the distal portion of the clamp lock member 304 to dip "downward, which releases the clamp mechanism assembly 410 from the clamp lock pocket 412. The release of the clamp mechanism assembly 410 from the clamp lock pocket 412 allows the jaw assembly to be freed from the clamp state. A closer view of the reset tab element 328 is illustrated in FIG. 5C. Also illustrated in FIG. 5C, in this first retracted or reset position, the deployment reset member 306 has not been engaged or reset by the reset tab element 306. The deployment reset member 306 has not engaged the ratchet member 310 and the mode switch button 352 has not been reset to neutral.

Figure 5D:
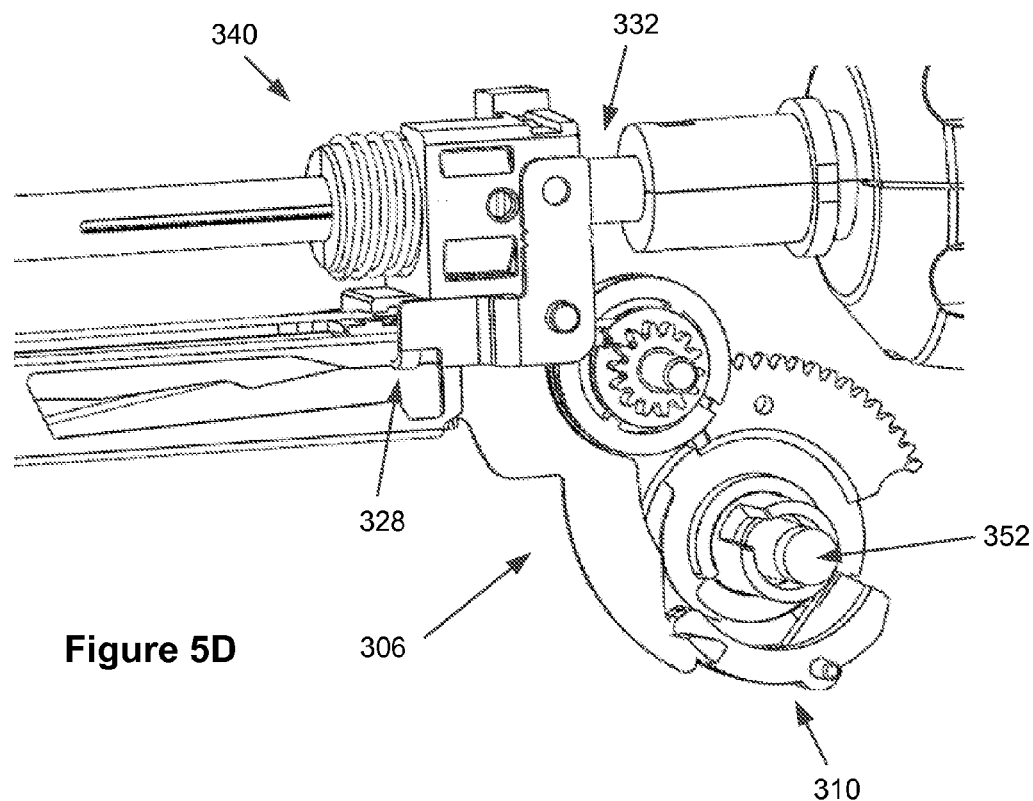
Figure 5E:
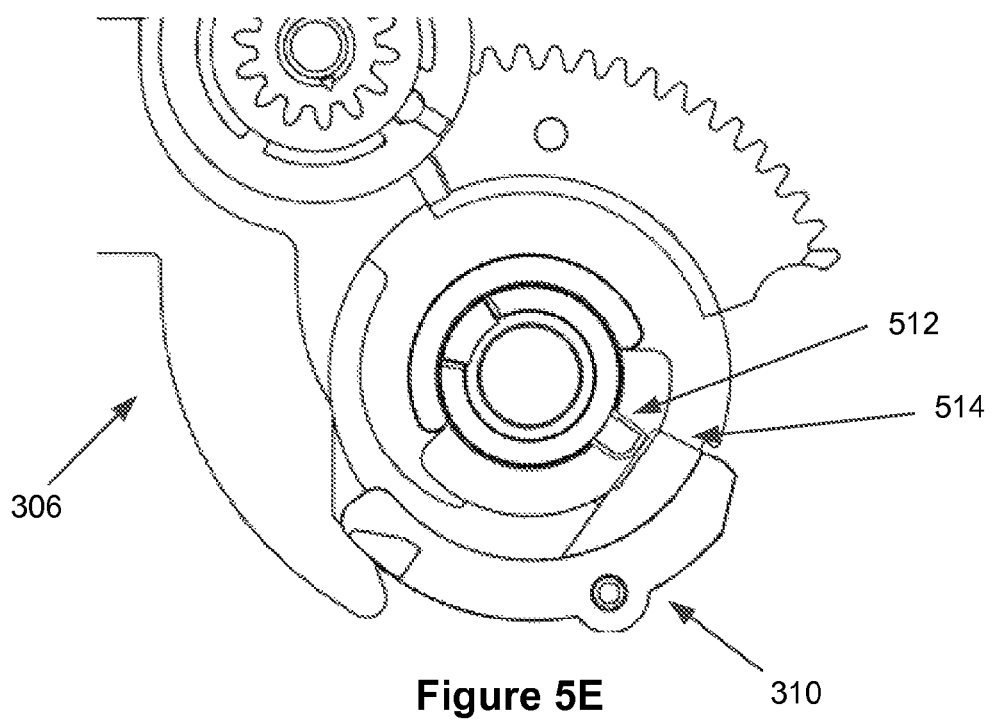
Figure 5F:
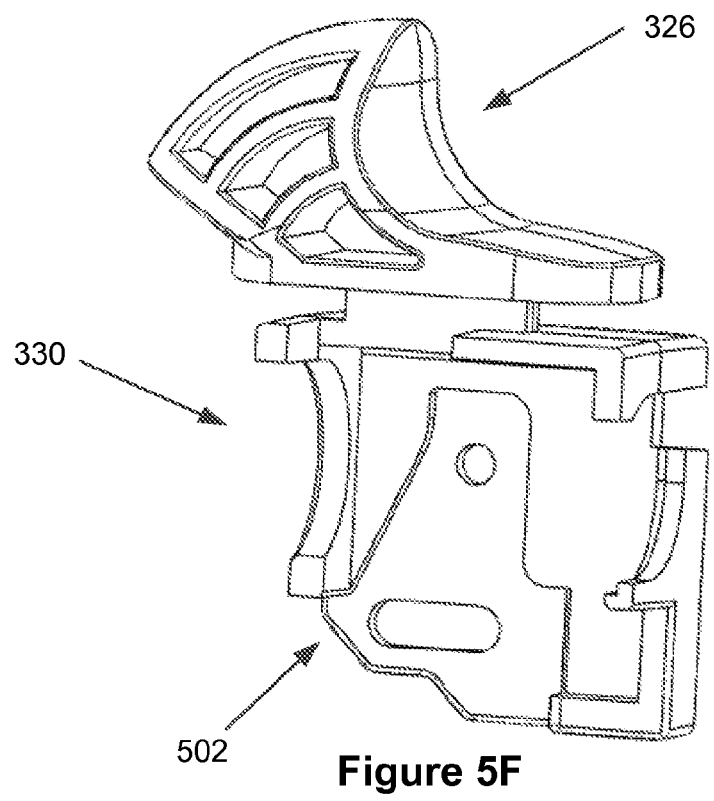
Figure 5G:
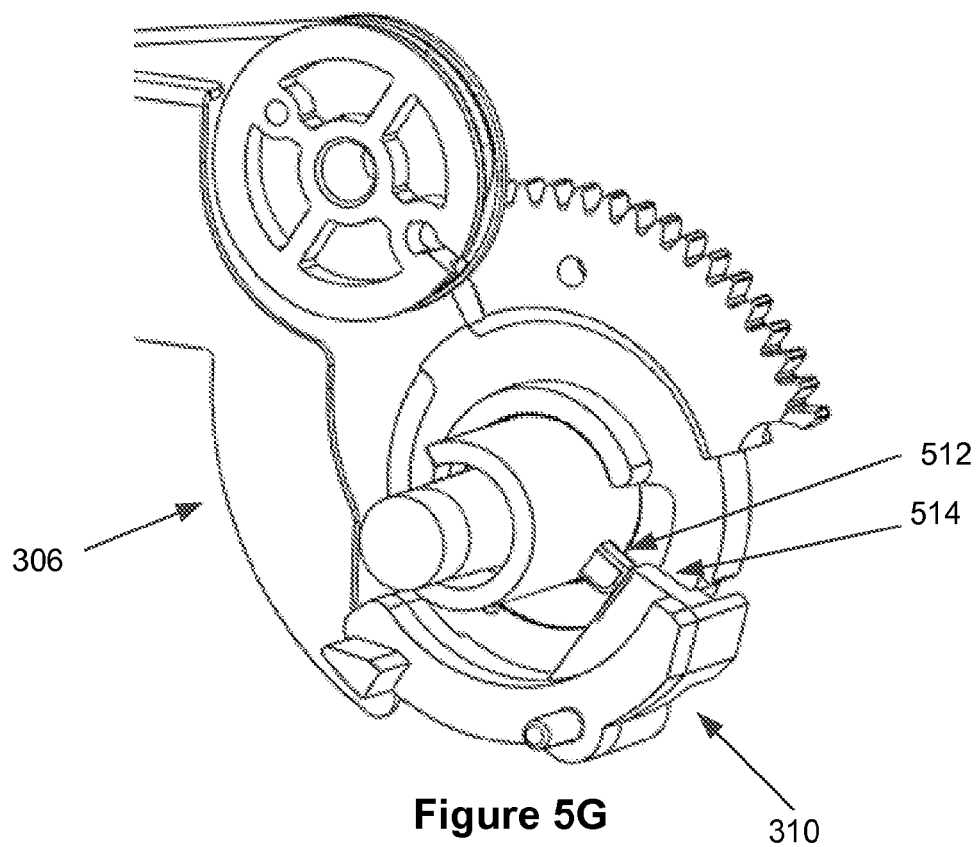
Figure 5H:
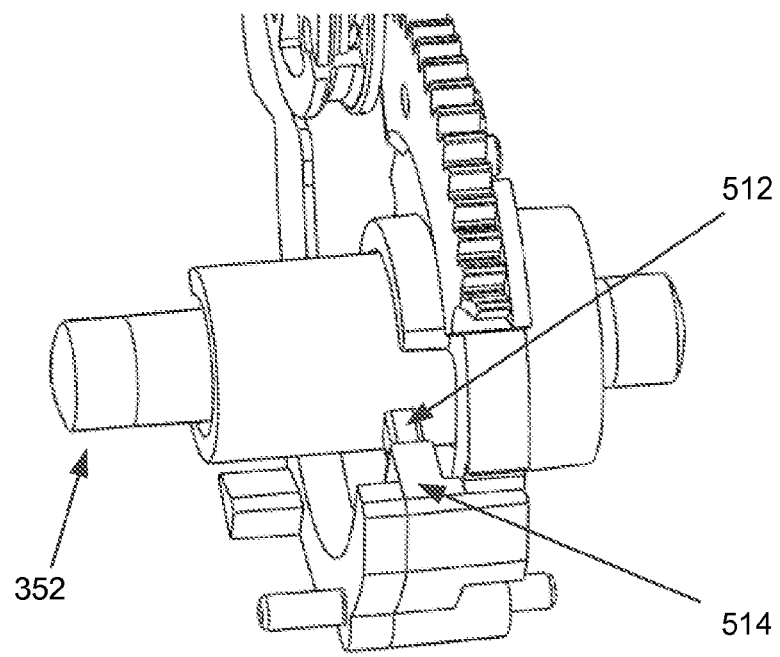

Referring to FIG. 5D, upon further retraction or pull of the reset handle 326 urges the deployment assembly 340 to a second retracted or reset position, compressing the spool member 324 spring element. In this second retracted or reset position, the swing arm member 332 is pivoted about the pivot pin 420 to a substantial horizontal position or orientation engaging the deployment reset member 306 which lifts the reset member 306 substantially upward. FIG. 5F illustrates that the deployment assembly cover member 330 includes various cut-outs, slots, or pathways to allow or facilitate pivoting or movement of the switch arm member 332. The upward movement of the reset member 306 engages with the ratchet member 310, as illustrated in FIG. 5E, which causes the ratchet member to shift or deflect. The movement of the ratchet member 310 allows the mode switch member 352 to reset to a neutral mode, which disengages the drive assembly 350 from the deployment mode to a neutral or un-deployment mode. The mode switch member may be spring loaded so that it can be self-actuated. The deployment assembly 340 may be maintained in a neutral mode by engagement of the mode switch member standoff element 512 with a ratchet standoff element 514, as further illustrated in FIG. 5G and FIG. 5H.

The various deployment systems, assemblies, components, and elements as described allow the surgical stapling and cutting device 100 to be set by a mode switch member 352 to select a deployment mode to engage a drive assembly 350 for deployment. A surgeon using the surgical device 100 can activate the trigger assembly 300 by squeezing the trigger 302 to drive the various gears, pulleys, cable, etc. of the drive assembly 350 to advance a deployment slide member 320 of a deployment assembly 340 and then to urge forward by the deployment assembly 340 a wedge assembly 220 to deploy staples 218 in a target tissue by a wedge element 224. The deployment assembly 340 also urges forward a knife member 116 to cut the target tissue. To reset deployment, a reset switch member 326 can pull or retract the deployment assembly 340 backward to place a swing arm member 332 in a first reset position to release a clamp lock member 304 to unclamp a jaw assembly. The deployment assembly 340 can be retracted or pulled back further to place the swing arm member 332 in a second reset position to release a deployment release member 306 to reset a mode switch member 352 to a neutral state to disengage the drive assembly 350 from deployment or the deployment mode. The surgical device is then placed in a neutral state, reset from the deployment mode, and is ready to be selected to a desired operational mode, such as a clamp mode or a deployment mode.

Multiple features, aspects, and embodiments of the invention have been disclosed and described herein. Many combinations and permutations of the disclosed invention may be useful in minimally invasive surgical procedures, and the invention may be configured to support various endo-cutters and/or stapling systems. One of ordinary skill in the art having the benefit of this disclosure would appreciate that the foregoing illustrated and described features, aspects, and embodiments of the invention may be modified or altered, and it should be understood that the invention generally, as well as the specific features, aspects, and embodiments described herein, are not limited to the particular forms or methods disclosed, but also cover all modifications, equivalents and alternatives. Further, the various features and aspects of the illustrated embodiments may be incorporated into other embodiments, even if not so described herein, as will be apparent to those ordinary skilled in the art having the benefit of this disclosure.

Although particular features, aspects, and embodiments of the present invention have been shown and described, it should be understood that the above discussion is not intended to limit the present invention to these features, aspects, and embodiments. It will be obvious to those skilled in the art that various changes and modifications may be made without departing from the spirit and scope of the present invention. Thus, the present invention is intended to cover alternatives, modifications, and equivalents that may be within the spirit and scope of the following claims and their equivalents.

What is claimed is:

1. A surgical stapling device, comprising:
   a handle assembly;
   a shaft assembly coupled to the handle assembly; and
   an end-effector coupled to the shaft assembly,
   wherein the end-effector comprises:
   a jaw assembly configured to clamp, staple, and cut a target tissue,
   wherein the handle assembly comprises:
   a trigger element to activate a drive assembly to advance a deployment assembly to staple and cut said target tissue,
   wherein the deployment assembly comprises:
   a deployment slide member to either advance said deployment assembly in a first direction or retreat said deployment assembly in a second direction, and
   a swing arm member movably coupled to said deployment assembly configured to reset a clamp lock member to release the jaw assembly to an un-clamp state, and said swing arm member to further reset a deploy release member to allow a mode switch member to be reset to a neutral state disengaging said drive assembly from a deploy mode.

2. The surgical stapling device of claim 1 wherein said swing arm member includes a reset tab element to engage said clamp lock member to reset said clamp lock member and said reset tab element also configured to engage said deploy release member.

3. A surgical stapling device, comprising:
   a mode switch member to select a drive assembly to a deployment mode;
   a trigger member to activate said drive assembly to advance a deployment assembly to staple and cut a target tissue;
   a deployment slide member to advance said deployment assembly in a first direction to drive both a wedge assembly to deploy staples into said target tissue and a knife member to cut said target tissue; and
   a swing arm member with a reset tab element to release a clamp lock to unclamp a jaw assembly to release said target tissue and to reset said mode switch member to a neutral state to disengage said drive assembly from the deployment mode.

4. A surgical stapling device, comprising:
   a mode switch member to select a drive assembly to a deployment mode;
   a trigger member to activate said drive assembly to advance a deployment assembly to staple a target tissue;
   a deployment slide member to advance said deployment assembly in a first direction to drive a wedge assembly to deploy staples into said target tissue; and
   a swing arm member with a reset tab element to release a clamp lock to unclamp a jaw assembly to release said target tissue and to reset said mode switch member to a neutral state to disengage said drive assembly from the deployment mode.

5. A method of stapling and cutting tissue by a surgical stapling device, comprising:
   setting a mode switch member to select a drive assembly to a deployment mode;
   activating a trigger member to drive said drive assembly;
   advancing a deployment slide member of a deployment assembly;
   urging forward by the deployment assembly a wedge assembly to deploy staples in a target tissue;

urging forward by the deployment assembly a knife member to cut said target tissue; and placing a swing arm member with a reset tab element in a first reset position to release a clamp lock to unclamp a jaw assembly.

6. The method of claim 5, further comprising:
placing said swing arm member in a second reset position to release a deployment release member to reset said mode switch member to a neutral state to disengage said drive assembly from deployment.

7. A surgical stapling device, comprising:
a handle assembly;
a shaft assembly coupled to the handle assembly; and
an end-effector coupled to the shaft assembly,
wherein the end-effector comprises:
a jaw assembly configured to clamp, staple, and cut a target tissue,
wherein the handle assembly comprises:
a trigger element to activate a drive assembly to advance a deployment assembly to staple and cut said target tissue,
wherein the deployment assembly comprises:
a deployment slide member to either advance said deployment assembly in a first direction or retreat said deployment assembly in a second direction, and
a reset switch member configured to retreat said deployment assembly to a first reset position causing an unclamp tab element of a swing arm member to release a clamp lock member from a clamp lock state.

8. The surgical stapling device of claim 7, wherein said reset switch further configured to retreat said swing arm member without displacing said deployment assembly to cause said unclamp tab element to engage a deployment release member to reset a mode switch member from a deployment mode.

9. A surgical stapling device, comprising:
a mode switch member to select a drive assembly to a deployment mode;
a trigger member to activate said drive assembly to advance a deployment assembly to staple and cut a target tissue;
a deployment slide member to advance said deployment assembly in a first direction to drive both a wedge assembly to deploy staples into said target tissue and a knife member to cut said target tissue; and
a reset switch member to place a swing arm member with a reset tab element in a first reset position to release a clamp lock member to unclamp a jaw assembly to release said target tissue.

10. The surgical stapling device of claim 9, wherein the reset switch member further places the swing arm member in a second reset position without causing displacement of the deployment assembly to release a deployment reset member.

11. A surgical stapling device, comprising:
a mode switch member to select a drive assembly to a deployment mode;
a trigger member to activate said drive assembly to advance a deployment assembly to staple a target tissue;
a deployment slide member to advance said deployment assembly in a first direction to drive a wedge assembly to deploy staples into said target tissue; and
a reset switch member to place a swing arm member with a reset tab element in a first reset position to release a clamp lock member to unclamp a jaw assembly to release said target tissue.

12. The surgical stapling device of claim 11, wherein the reset switch member further place the swing arm member in a second reset position without causing displacement of the deployment assembly to release a deployment reset member.

13. A method of stapling and cutting tissue by a surgical stapling device, comprising:
setting a mode switch member to engage a drive assembly to a deployment mode;
activating a trigger member to drive said drive assembly;
advancing a deployment slide member of a deployment assembly;
urging forward by the deployment assembly a wedge assembly to deploy staples in a target tissue;
urging forward by the deployment assembly a knife member to cut said target tissue; and
placing a swing arm member with a reset tab element in a first reset position to release a clamp lock to unclamp a jaw assembly.

14. The method of claim 13, further comprising:
placing said swing arm member in a second reset position, without causing displacement to the deployment assembly, to release a deployment release member to reset said mode switch member to a neutral state to disengage said drive assembly from deployment.

15. The method of claim 14, further comprising:
placing said swing arm member in a second reset position release a clamp lock to unclamp a jaw assembly to disengage said target tissue.

16. A surgical stapling device, comprising:
a handle assembly;
a shaft assembly coupled to the handle assembly; and
an end-effector coupled to the shaft assembly,
wherein the end-effector comprises:
a jaw assembly configured to clamp, staple, and cut a target tissue,
wherein the handle assembly comprises:
a trigger element to activate a drive assembly to advance a deployment assembly to staple and cut said target tissue,
wherein the deployment assembly comprises:
a deployment slide to either advance said deployment assembly in a first direction or retreat said deployment assembly in a second direction, and
a reset switch member configured to retreat said deployment assembly to a first reset position causing an unclamp tab element of a swing arm member to engage a deployment release member to reset a mode switch button from a deployment mode.

17. The surgical stapling device of claim 16, wherein said reset switch further configured to retreat said swing arm member to cause said unclamp tab element to engage a clamp lock member from a clamp lock state to release said jaw assembly from a clamped state.

18. The surgical stapling device of claim 16, wherein said deployment release member include stepwise features or ramp-wise features to engage with said unclamp tab element of said swing arm member.

19. A surgical stapling device, comprising:
a mode switch member to select a drive assembly to a deployment mode;
a trigger member to activate said drive assembly to advance a deployment assembly to staple and cut a target tissue;
a deployment slide member to advance said deployment assembly in a first direction to drive both a wedge assembly to deploy staples into said target tissue and a knife member to cut said target tissue; and a reset switch member to place a swing arm member with a reset tab element in a first reset position to release a deployment reset member.

20. The surgical stapling device of claim 19, wherein the reset switch member further places the swing arm member in a second reset position to release a clamp lock member to unclamp a jaw assembly to release said target tissue.

21. A surgical stapling device, comprising:
a mode switch member to select a drive assembly to a deployment mode;
a trigger member to activate said drive assembly to advance a deployment assembly to staple a target tissue;
a deployment slide member to advance said deployment assembly in a first direction to drive a wedge assembly to deploy staples into said target tissue; and
a reset switch member to place a swing arm member with a reset tab element in a first reset position to release a deployment reset member.

22. The surgical stapling device of claim 21, wherein the reset switch member further places the swing arm member in a second reset position to release a clamp lock member to unclamp a jaw assembly to release said target tissue.

23. A method of stapling and cutting tissue by a surgical stapling device, comprising:
setting a mode switch member to engage a drive assembly to a deployment mode for deployment;
activating a trigger member to drive said drive assembly;
advancing a deployment slide member of a deployment assembly;
urging forward by the deployment assembly a wedge assembly to deploy staples in a target tissue;
urging forward by the deployment assembly a knife member to cut said target tissue; and
placing a swing arm member with a reset tab element in a first reset position to release a deployment release member to reset said mode switch member to a neutral state to disengage said drive assembly from deployment.

* * * * *